United States Patent [19]
Kirk et al.

[11] Patent Number: 5,798,035
[45] Date of Patent: Aug. 25, 1998

[54] HIGH THROUGHPUT SOLID PHASE CHEMICAL SYNTHESIS UTILIZING THIN CYLINDRICAL REACTION VESSELS USEABLE FOR BIOLOGICAL ASSAY

[75] Inventors: Gregory L. Kirk, Skillman, N.J.; Robert H. Grubbs, South Pasadena, Calif.

[73] Assignee: Pharmacopeia, Inc., Princeton, N.J.

[21] Appl. No.: 726,058

[22] Filed: Oct. 3, 1996

[51] Int. Cl.⁶ ................................................. C25B 15/02
[52] U.S. Cl. ................. 205/335; 422/55; 422/56; 422/57; 422/59; 422/63; 422/82; 422/119; 422/129; 422/138; 422/188; 422/196; 422/197; 422/232; 422/233; 422/236; 436/52; 436/55; 436/47; 436/48; 436/49; 436/165; 436/169; 206/305; 206/459.5
[58] Field of Search ................... 422/55, 56, 57, 422/58, 59, 63, 82, 119, 129, 138, 188, 196, 197, 232, 233, 234, 236; 206/568, 569, 305, 459.5; 436/44, 52, 55, 47, 48, 49, 165, 169, 523, 527, 528, 518, 531, 535; 205/335

[56] References Cited

U.S. PATENT DOCUMENTS

| | | | |
|---|---|---|---|
| 3,531,258 | 9/1970 | Merrifield et al. | 23/252 |
| 3,951,741 | 4/1976 | Pfaender et al. | 195/29 |
| 4,252,769 | 2/1981 | Hood et al. | 422/50 |
| 4,351,762 | 9/1982 | Verlander et al. | 260/112.5 R |
| 4,362,699 | 12/1982 | Verlander et al. | 422/131 |
| 4,552,922 | 11/1985 | Patchornik et al. | 525/54.11 |
| 4,631,211 | 12/1986 | Houghten | 428/35 |
| 4,746,490 | 5/1988 | Saneii | 422/62 |
| 4,800,166 | 1/1989 | Horn et al. | 436/55 |
| 4,816,513 | 3/1989 | Bridgham et al. | 525/54.11 |
| 4,861,866 | 8/1989 | Durrum et al. | 530/333 |
| 5,102,986 | 4/1992 | Coffey et al. | 530/334 |
| 5,169,935 | 12/1992 | Hoeger et al. | 530/328 |
| 5,186,898 | 2/1993 | Bridgham et al. | 422/102 |
| 5,188,733 | 2/1993 | Wang et al. | 210/321.84 |
| 5,202,418 | 4/1993 | Lebl et al. | 530/334 |
| 5,258,454 | 11/1993 | Berg et al. | 525/54.11 |
| 5,286,789 | 2/1994 | Okrongly et al. | 525/54.11 |
| 5,318,679 | 6/1994 | Nishioka | 204/157.68 |
| 5,324,483 | 6/1994 | Cody et al. | 422/131 |
| 5,338,831 | 8/1994 | Lebl et al. | 530/334 |
| 5,384,261 | 1/1995 | Winkler et al. | 436/518 |
| 5,387,526 | 2/1995 | Garner et al. | 436/169 |
| 5,609,826 | 3/1997 | Cargill et al. | 422/196 |
| 5,612,002 | 3/1997 | Cody et al. | 422/196 |
| 5,663,545 | 9/1997 | Marquiss | 422/104 |

FOREIGN PATENT DOCUMENTS

| | | |
|---|---|---|
| 1312991 | 1/1993 | Canada. |
| 0 274 999 A2 | 12/1987 | European Pat. Off.. |
| 0 355 266 A2 | 4/1989 | European Pat. Off.. |
| WO 88/05074 | 7/1988 | WIPO. |
| WO 92/00091 | 1/1992 | WIPO. |
| WO 92/22591 | 12/1992 | WIPO. |
| WO 93/02992 | 2/1993 | WIPO. |
| WO 93/05065 | 3/1993 | WIPO. |
| WO 93/12427 | 6/1993 | WIPO. |
| WO 93/17056 | 9/1993 | WIPO. |
| WO 94/05394 | 3/1994 | WIPO. |
| WO 94/08051 | 4/1994 | WIPO. |

OTHER PUBLICATIONS

Chemical Abstracts, vol. 105, 1986; Abstract No. 97882m; vol. 104, 1986 Abstract No. 1 86857d. No Month Available.
Chemical Abstracts, vol. 88, 1978; Abstract No. 170484v. No Month Available.
Chemical Abstracts, vol. 76, 1972, Abstract No. 72776z.; vol. 77, 1972, Abstract No. 34910b. No Month Available.
Chemical abstracts, vol. 103, 1985, Abstract Nos. 178611h; 196394u. No Month Available.
Chemical Abstracts, vol. 83, 1975, AbstractNo. 43731v. No Month Available.
Chemical Abstracts, vol. 66, 1967, Abstract No. 18845b. No Month Available.
Chemical Abstracts, vol. 122, 1995, Abstract No. 10543f.; Abstract No. 10640k; Abstract No. 31956h No Month Available.
Chemical Abstracts, vol. 108, 1988, Abstract No. 222106b; Abstract No. 120766z. No Month Available.
Chemical Abstracts, vol. 117, 1992, Abstract No. 234542q. No Month Available.
Chemical Abstracts, vol. 118, 1993, Abstract No. 148037t.; Abstract No. 148052u. No Month Available.
Chemical Abstracts, vol. 119, 1993, Abstract No. 117846x. No Month Available.

(List continued on next page.)

*Primary Examiner*—Bruce F. Bell
*Attorney, Agent, or Firm*—Heslin & Rothenberg, P.C.

[57] ABSTRACT

A high throughput chemical synthesis system utilizing cylindrical reaction vessels is disclosed. Reaction vessels are utilized which include a tubular member adapted for placement of electronically readable identifying indicia thereon. The identifying indicia are representative of reaction conditions within the tubular member and of one or more reagents utilized in a reaction within the tubular members. A method of performing chemical synthesis on solid phase reactive material within a plurality of reaction vessels using a plurality of reaction stages resulting in final products and employing identifying indicia representing the reaction stages is also disclosed. The method includes reading the identifying indicia located on the reaction vessels, reacting one or more reagents within the reaction vessels under particular reaction conditions which may be determined by reading the identifying indicia, thereby synthesizing chemical compounds within the reaction vessels. The method allows chemical synthesis to occur according to a predetermined set of reactions and also allows for combinatorial chemistry to be performed utilizing random mix and split techniques. The final synthesized products may be tested for chemical or biological activity. The chemical structures of desired end products may be obtained by reading recorded information wherein the reaction conditions and reagents of reaction steps have been recorded, preferably in conjunction with the identifying indicia.

78 Claims, 8 Drawing Sheets

OTHER PUBLICATIONS

Chemical Abstracts, vol. 121, 1994, Abstract No. 281191s. No Month Available.

Chemical Abstracts, vol. 106, 1987, Abstract No. 33451h; Abstract No. 52280t; Abstract No. 156848a No Month Available.

Chemical Abstracts, vol. 107, 1987, Abstract No. 7530j; vol. 109, 1988, Abstract Nos. 190792z; 190800a. No Month Available.

Chemical Abstracts, vol. 110, 1989, Abstract Nos. 58014p; 127789j; vol. 111, 1989, Abstract No. 58282v. No Month Available.

Chemical Abstracts, vol. 112, 1990, Abstract Nos. 99271e; 237306y. No Month Available.

Chemical Abstracts, vol. 113, 1990, Abstract Nos. 41334g; 115836w; vol. 97, 1982, Abstract No. 24208c. No Month Available.

Chemical Abstracts, vol. 114, 1991, Abstract Nos. 43554y; 62733x; 207784b. No Month Available.

Chemical Abstracts, vol. 115, 1991, Abstract Nos. 29887y; 67673h; 183890a; 183891b. No Month Available.

Chemical Abstracts vol. 101, 1984, Abstract No. 73078v; vol. 102, 1985 Abs. No. 149758k.

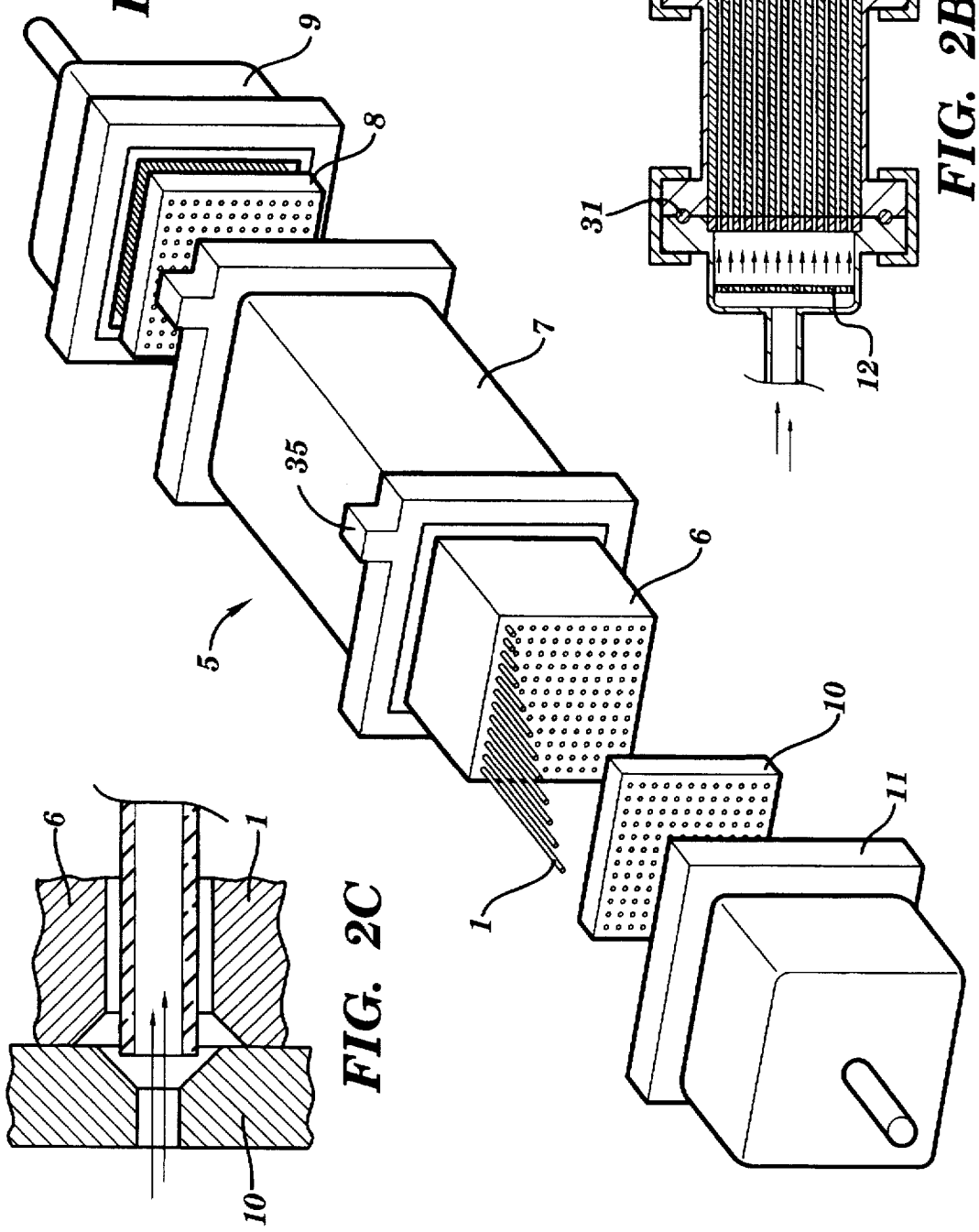

HIGH THROUGHPUT SOLID PHASE CHEMICAL SYNTHESIS UTILIZING THIN CYLINDRICAL REACTION VESSELS USEABLE FOR BIOLOGICAL ASSAY

FIELD OF THE INVENTION

This invention relates to the field of combinatorial chemistry and, more particularly, to a technique for performing combinatorial chemistry using high throughput solid phase chemical synthesis within a plurality of thin elongate reaction vessels.

DESCRIPTION OF RELATED ART

Combinatorial chemistry involves the synthesis of a large variety of chemical compounds from a series of reactions or "chemical recipes". Various combinatorial chemistry techniques have been used to create a large number or library of compounds and these large numbers of compounds can then be screened for various possible biological activities for pharmaceutical, agricultural or other purposes. Typically such a synthesis occurs in successive stages, each of which involves a chemical modification of the then existing molecules.

Geysen, in PCT Patent Appln. No., WO 90/09395 describes an approach to high-throughput synthesis of peptide oligomers by synthesizing these structures as they are attached to an array of "pins" that are dipped into different reaction mixtures. However, using this approach, quantities of synthesized compounds are limited. U.S. Pat. No. 5,143,854 to Fodor et al. discloses a similar array synthesis method for peptides, oligonucleotides, and perhaps other oligomers by using lithographic techniques derived from the semiconductor industry, but applied to synthetic chemistry. Again, using these techniques, yields are limited, typically to subpicomoles, chemistries are also limited by the lithographic technique, and biological activities must be assessed on the lithographic array.

The concept of bead-based split synthesis to make large collections of oligomers was first disclosed by Furka et al. in the 14th Int'l Congress of Biochemistry, Prague, Czechoslovakia, Jul. 15, 1988. A mix and split methodology is used whereby solid phase reactive materials are randomly mixed and separated between reaction stages. The reactive materials are then exposed to reactive agents and conditions which are tracked. Dower et al. in PCT Patent Appln. No. WO 93/06121, also disclose a "split synthesis" methodology for synthesizing large numbers of different oligomers while they are attached to bead-based solid phase supports as disclosed by Merrifield in *Science*, vol. 236, Apr. 18, 1986, pgs 341–347. The oligomers on each bead can be identified directly or indirectly using an oligonucleotide "tag" that tracks each synthetic step. However, the quantity available on each bead is generally less than 1 nanomole and the process of identifying compounds involves PCR or some other tedious chemical method.

Still et al. in PCT Patent International Publ. No. WO 94/08051 have disclosed an improved bead-based split synthesis technique which includes a wide variety of chemical reactions not limited to oligomers. The beads disclosed by Still et al. are also "tagged," but with a binary code utilizing independent chemical entities that are more readily detected and identified using Gas Chromatography techniques. Nonetheless, the quantities of synthetic compound yielded from this technique are still subnanomole and their identification is still based on chemical methods.

Houghten in European Patent Appln. No. 196174, describes yet another method applicable to the synthesis of peptides or oligonucleotides where solid support resin beads are partitioned using inert plastic mesh bags or "tea-bags" where they stay together during synthesis. Many "tea-bags" can be processed using split synthesis to generate sufficient quantities of an array of compounds. The methods as described by Houghten are specific to oligomeric reactions. However, others, like Cody et al., in U.S. Pat. No. 5,324,483, have generalized the basic "tea-bag" principle to include segregating beads during reactions in systems that are compatible with a wide range of chemical reactions. However, these systems are somewhat awkward to use, require that the beads be agitated, require many fluid-tight seals that must allow removal and insertion and may require physically large layout areas for a reasonable number of distinct compounds. In addition, detachment of compounds and delivery to bioassays would be cumbersome for large numbers of compounds.

Others such as Pavia et al., as disclosed in Bioorganic & Medicinal Chem. Letters, (1993), vol. 3, pgs. 387–396 have used robotic or automated systems for the synthesis of compounds in liquid or solid phase (e.g., on beads) with milligram quantities possible and some economies gained. All of these robotic systems allow reasonably flexible programming of parallel synthesis of an adequate quantity of compounds in separate reaction wells. However, these systems are essentially serial in nature and do not enjoy the enormous advantages of the split synthesis methods described above. Operation is generally limited to hundreds or thousands of compounds, and the automation can add extra constraints on the choices or efficiencies of the synthetic reaction steps used. Moreover, the solid phase bead-based systems require agitation as mentioned above.

Beattie et al., in U.S. Pat. No. 5,175,209 and Frank et al., in U.S. Pat. No. 4,689,405 describe a method of synthesizing oligomers in large quantities using mix and split techniques similar to those described above where solid support structures in the form of disks are sorted into reaction vessels and resorted after each step. The identity of the oligomer on each disk is defined by the reaction chamber in which such disk was located during each reaction step. Since the disks are large and can be marked, the sorting is deliberate and direct. Moreover, non-chemical (e.g., mechanical) methods may be used to mark and identify the disks as they go through each synthesis step and thereby identify the structures thereon. The quantities achievable using this method are greater than 1 mg. However, the methods described by Beattie et al. and Frank et al. are specific to oligomers, and the disk support structures do not provide a convenient interface to standard bioassays such as 96-well-plate-based tests. Compounds in solutions extracted from these disks are not easily loaded into standard 96-well plates. The sorting and loading methods for the disks may also be inadequate if the numbers of different structures desired reaches 100,000 or more. Moreover, the mesh-like solid supports described by Beattie et al. and Frank et al. may not be applicable to non-oligomeric chemistries.

Therefore, none of these methods is ideal for synthesizing greater than milligram quantities of non-oligomeric chemical compounds in combinatorial or otherwise large libraries in such a way that sampling such libraries into 96-well plates or other standard bio-assay formats is easily achieved.

It is therefore desirable to obtain a combinatorial chemical library synthesis system which is capable of a wide variety of synthetic operations creating medicinally relevant molecules as well as biopolymers.

It is also desirable to obtain a combinatorial chemical library synthesis system which provides a yield in excess of 1 milligram for each compound in the library with reasonable purity.

It is further desirable to obtain a system of executing combinatorial "mix and split" synthetic strategies for up to 100,000 distinct elements. Such a system should provide for random as well as deliberate mixing, which is important when one desires to reduce the library from the set of all combinations because of chemical or other constraints.

It is further desirable to obtain a combinatorial chemical library synthesis system which conveniently prepares samples for biological screening while allowing for quantitative partial extraction and compatibility with 96-well or high density screening formats.

It is also desirable to provide a combinatorial chemical library synthesis system which facilitates the deliberate sorting and selecting of library members.

SUMMARY OF THE INVENTION

The present invention provides all of the above desirable aspects, and a goal of the present invention is to provide a method of synthesizing a large variety of potentially novel organic compounds from a systematic scheme of "chemical recipes"(i.e., to perform combinatorial chemistry) with sufficient yield (>1 μmol or >1 mg) and purity to allow a wide range of tests that would enable discovery of drugs, agrochemicals, or specialty chemicals from this set of organic structures. In the case of drug discovery, these tests would include standard assay formats in the areas of microbiology, enzymology, biological receptor binding studies, toxicology, etc.

The present invention also has the advantage of providing a convenient means to facilitate delivery of chemical samples to typical testing formats (e.g. 96-well or higher density arrays of vessels used in bio-tech laboratories).

The present invention also provides convenient and reliable means to track the identity of each compound during the synthesis, sampling and testing process to facilitate detailed studies of chemical structure vs. biological activity relationships (QSAR). Improved tracking and control of samples during synthesis also increases the flexibility in designing such "combinatorial libraries."

The aforementioned advantages may be achieved by use of a high throughput solid phase chemical synthesis system using thin tubular, and preferably cylindrical, reaction vessels.

In the present invention, a single reaction vessel may include a straight, coaxial tubular member. The tubular member may be adapted for placement of electronically readable identifying indicia thereon so as to represent reaction conditions which have occurred or which will occur within the tubular member and reagents utilized in such reactions. As used herein, the term "electronically readable" includes optically readable.

The identifying indicia may comprise a bar code which may be formed by a series of readable bars which extend around the outer circumference at a first end of the tubular member. The tubular member may be coated with a defined thickness of a solid phase reactive material on an inside surface thereof. Alternatively, the reaction vessel may contain an elongated rod, coaxially oriented within the tubular member, which is coated with such a reactive material. The solid phase materials may be in the form of a gel that is swellable in a variety of solvents and which has reactive sites distributed throughout the volume thereof. As yet another alternative, the reaction vessel may be filled with a plurality of solid phase reactive beads which are retained therein by frits located at the ends of the tubular member.

The present invention further includes a system which allows chemical synthesis to be performed on solid phase reactive material disposed within one or more reaction vessels, using one or more reaction stages, resulting in one or more final products and employing identifying indicia for each reaction vessel to represent the specific reactions and reagents utilized during each reaction stage in each vessel. The method employed in such system may include reading the identifying indicia of a tubular reaction vessel having the reactive material therein, reacting a reagent within the reaction vessel under particular reaction conditions, and subsequently determining such reagent and reaction conditions by reading the identifying indicia, so as to identify the compound so synthesized. The aforementioned steps may be repeated at least once, thereby synthesizing and identifying chemical compounds within the reaction vessel. Information concerning the reagent and/or reaction conditions may be recorded in conjunction with information concerning the identifying indicia. When recorded, information concerning the reagent or reaction conditions may correspond to particular indicia so that when particular indicia are read, the corresponding information concerning the reagent or reaction conditions used in a particular reaction vessel may be readily determined.

The tubular reaction vessels may be marked with the identifying indicia thereon and any of the reaction vessel embodiments previously discussed supra may be used within this method. In addition, the tubular reaction vessels may be adapted for insertion, individually or in a group, into a reaction chamber wherein the reacting steps are performed, in parallel, in each such reaction vessel in the group. The reaction steps may include flowing a reagent-containing solution through groups of such tubular reaction vessels within one or more reaction chambers so as to communicate with the solid phase reactive material therein, effectively accessing all binding sites within such reactive material. The tubular reaction vessels in the group may be removed from the reaction chamber and sorted by reading the identifying indicia, such as a bar code, thereon. The reaction vessels may be pooled and/or sorted into two or more new groups, and each group then inserted into a separate reaction chamber.

In addition, the system allows for the random mixing and separating of the reaction vessels after one or more reaction steps, which may be performed when creating combinatorial libraries. For example, a group of reaction vessels may be removed from several reaction chambers, mixed and randomly separated into two or more groups for delivery to different reaction chambers for different subsequent reactions. After these reactions, additional random mixing and separating, as well as additional reactions may occur. Data relating to the reactions, e.g., reagents and reaction conditions, may be reflected by the reaction vessels' identifying indicia, e.g., bar codes. These identifying indicia may be read, e.g., electronically, immediately prior to or after a reaction step has occurred. Such indicia, along with the specific reaction step information corresponding thereto, may be recorded and stored, e.g., in a database. The reaction history of each individual reaction vessel can therefore be tracked, and the chemical recipe determined for the compounds synthesized, respectively, within each vessel.

In the random synthesis just described, unless multiple copies of each reaction product are made, there is a likelihood that not all members of the set of potential final products will be synthesized. Therefore, in accordance with the invention, solid phase chemical synthesis also may be performed according to a pre-selected chemical recipe performed on reactive material within a plurality of tubular reaction vessels, resulting in the synthesis of either the complete set of all possible combinations of a set of reagents in a series of reactions or a predetermined subset thereof in a predetermined number of copies, e.g., one copy. The method includes reading coded indicia located on the reaction vessels, reacting one or more reagents within the reaction vessels under particular reaction conditions where the reagents and reaction conditions subsequently are determined by the reading of the coded indicia, and repeating the reading and reacting steps until the desired chemical compounds have been synthesized within the reaction vessels, the identities of such compounds being readily ascertainable from reading the coded indicia. When the reacting step is repeated, in accordance with this "pre-selected recipe method," the reaction vessels may be deliberately sorted into reaction chambers to undergo specific reactions represented by the indicia. The chemical recipe of each chemical compound corresponds to particular pre- or post-coded indicia on the reaction vessel wherein its synthesis occurred.

The present system also facilitates synthesizing chemical or biological compounds for direct delivery to an assay. The synthesized compounds may be attached to the solid phase reactive material by photo-labile covalent linking techniques, in which case the tubular reaction vessels may be exposed to a controlled intensity light source to release synthesized compounds from the reactive material for elution with appropriate solvents. The resulting eluent (i.e., compound dissolved in solvent) remains in the reaction vessel and is available for delivery to a bioassay. Such synthesized chemical compounds may be transferred directly from the reaction vessels into a plurality of assay wells. Alternative chemical methods can be used to detach compounds, e.g., by adding, neutralizing, and removing detachment reagents. The synthesized chemical compounds may be screened for biological, chemical, agricultural or other purposes. The method may be performed in parallel on multiple reaction vessels having different solid phase reactive materials therein. Optionally, before detachment of a synthesized chemical compound, a reaction vessel may be separated, e.g., "cut-up," into multiple pieces for use in multiple assays.

The method employed in such direct delivery system includes performing a plurality of reaction steps on the reactive material within each of a plurality of tubular reaction vessels. After one or more such reaction steps, the reaction vessels may be mixed and separated into one or more groups. Each group of reaction vessels may then be placed into a different reaction chamber where the reactive materials therein will be exposed to different reactions. Data relating to the reactions, e.g., reaction conditions and reagents, may be recorded in such a manner as to be identified with the particular reaction vessel. For example, for each of the reaction vessels, data relating to each reaction may be recorded and stored on in a database along with the reaction vessel's bar code, identifying the chemical recipe for the synthesized compound within. (It also is possible to track the reactions by recording the location of each reaction vessel in a particular reaction chamber for each reaction step and subsequently corresponding this data to other recorded data relating to the reaction conditions for each reaction chamber.) After all the reaction stages are completed, the reaction vessels are sorted into a transfer array based upon the identifying indicia, and a portion of the compound within each of the sorted reaction vessels may be removed therefrom for delivery to an assay plate or to a lawn-type assay. The compounds subsequently can be tested and the chemical recipe for desired (i.e., active) compounds obtained by matching their respective positions in the assay plate with the identifying indicia on the reaction vessels in the corresponding positions in the transfer array.

The present invention also facilitates the testing of synthesized compounds for biological or chemical activity. The tested compounds are synthesized during multiple reaction stages on solid phase reactive material contained within the reaction vessel prior to any testing. The testing may include transferring synthesized compounds from the tubular reaction vessels into a testing medium, the reaction vessels comprising electronically readable identifying indicia thereon representing reaction conditions which have occurred within the tubular reaction vessels. The synthesized compounds are then tested for a desired biological or chemical activity. By electronically reading the identifying indicia on the reaction vessel wherein was synthesized a compound having the desired biological or chemical activity, the method of synthesis of such compound (and, consequently, the structure of such compound) may be determined by looking up recorded information wherein specific identifying indicia correspond with specific reaction histories.

The present invention also encompasses an apparatus for performing chemical synthesis by performing a series of reactions on solid phase reactive material within a plurality of tubular reaction vessels, and one or more reaction chambers adapted to receive, individually or in a group, the tubular reaction vessels therein. Each of the reaction chambers has an inlet disposed to allow reagents to flow into the reaction chamber and into the reaction vessels disposed within the reaction chamber.

One or more guide arrays may be adapted for insertion into the reaction chambers and also adapted to receive the tubular reaction vessels therein. Each reaction chamber may have an inlet and an outlet located within a first and second reaction chamber cover, respectively. A guide cap having a plurality of apertures therein may be located between the inlet and the guide array so that the apertures are aligned with the reaction vessels to allow fluid reagents to flow, in parallel fashion, from the inlet to the respective reaction vessels within the reaction chamber. A second guide cap having a plurality of apertures therein may be located between the guide array and the outlet of the reaction chamber so that the apertures are aligned with the reaction vessels to allow fluid reagents to flow, in parallel fashion, from the respective reaction vessels to the outlet of the reaction chamber.

One or more reaction chambers may be placed in fluid flow relationship to an array valve which is in fluid flow relationship with a plurality of reservoirs each having reagents therein. The array valve is capable of distributing the reagents within the reservoirs to the plurality of the reaction chambers in various combinations. One or more pumps may be placed in fluid flow relationship between the array valve and each of the reaction chambers. Temperature control enclosures may be used to surround each of the reaction chambers to allow reactions to occur within specific temperature ranges.

An extrusion means such as a tool or other device may be used to remove the reaction vessels from the reaction chambers. The extrusion means may be adapted for insertion into the reaction chambers and for contact with individual reaction vessels therein. A sorting means receives the reaction vessels extruded from the reaction chambers and sorts the reaction vessels into one or more groups, to be determined based on the particular reaction or reactions to be performed within the reaction vessel. The sorting means may include a reader adapted to read identifying indicia, such as a bar code, on the reaction vessel. The sorting means may also include means for removing the extruded reaction vessels from a hopper which collects the reaction vessels after extrusion from the reaction chamber. A ramp or belt may be used to move the extruded reaction vessels to a vessel director disposed to load one or more reaction vessels into a vessel loading device. The vessel loading device is adapted to receive a reaction chamber and guide array therein and is moveable along a first and second axis to allow insertion of any reaction vessel in a particular location within the reaction chamber. A means for receiving one or more extruded reaction vessels from the sorting means, such as a robotic pipettor adapted to a vessel transfer array (described above), may be used to communicate with the reaction vessels and deposit synthesized compounds eluted therefrom into a plurality of wells of, e.g., a 96-well plate, or onto a lawn bioassay plate.

BRIEF DESCRIPTION OF THE DRAWINGS

FIG. 2A depicts a schematic representation of a preferred embodiment of a reaction chamber containing a plurality of reaction vessels;

FIG. 2B depicts a schematic representation of the reaction chamber shown with reaction fluids moving therethrough;

FIG. 2C depicts a sectional view from the side of a portion of the interface between an inlet guide cap and guide array insert, located within a reaction chamber, having a reaction vessel therein;

DETAILED DESCRIPTION OF THE PREFERRED EMBODIMENT

Figure 1A:
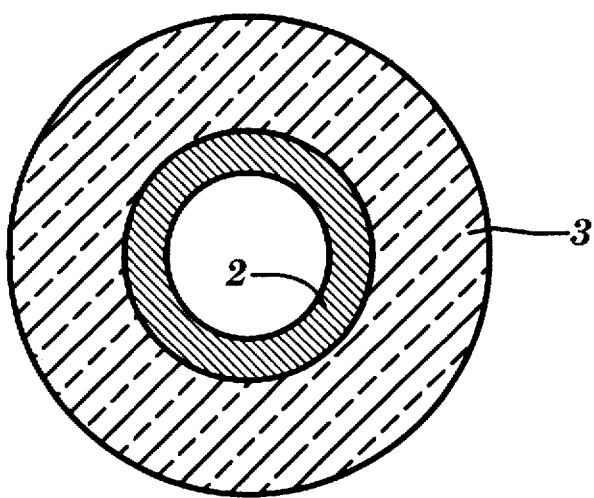
FIG. 1A depicts a top sectional view of a preferred embodiment of a disposable reaction vessel adapted for synthesis of a single compound therein.
Figure 1B:
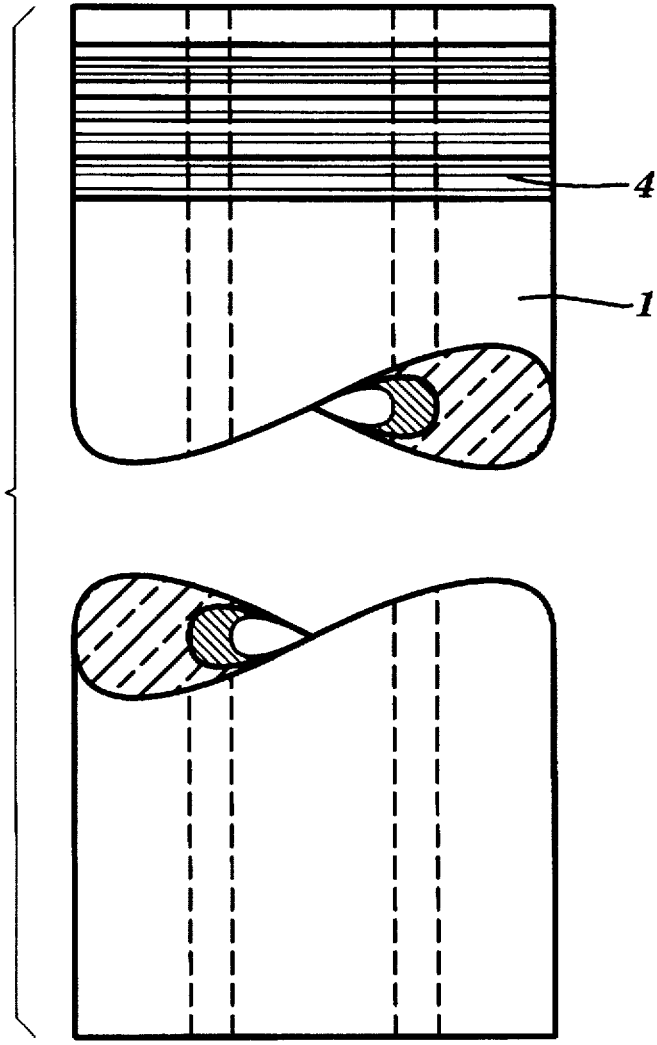
FIG. 1B depicts a cut-away sectional view from the side of the reaction vessel of FIG. 1A.

Referring to FIG. 1A and 1B, a preferred reaction vessel 1 is shown. The reaction vessel 1, which is preferably disposable, is one component of a system for performing solid phase chemical synthesis in accordance with the principles of the present invention. Each vessel contains an inner reactive coating 2 (or inner reactive packing—see discussion of FIG. 7 below) to which molecules of a synthesized compound are attached, throughout the volume thereof, during such synthesis. Typically, the coatings or packings are chemical polymers such as cellulose, pore-glass, silica gels, polystyrene optionally cross-linked with divinylbenzene and optionally grafted with polyethylene glycol and optionally functionalized with amino, hydroxy, carboxy, or halo groups, grafted co-poly beads, polyacrylamide beads, latex, dimethylacrylamide optionally cross-linked with N,N'-bis-acryloyl ethylene diamine, glass coated with hydrophobic polymers, etc. Preferably, the coating or packing is divinylbenzene-cross-linked, polyethyleneglycol-grafted polystyrene optionally functionalized with amino groups (for example, TentaGel® S $NH_2$, Rapp Polymere).

The outer shell 3 of the reaction vessel 1 is a structural element shaped such as a capillary tube, that provides an attachment surface, protects the polymer coating 2 and provides a rigid shape and defined size to the vessel 1. Although the tubular reaction vessel 1 is preferably thin and cylindrical in shape, other shapes and configurations may be used. For example, instead of a cylinder shape, other polygonally shaped tubular structures may be used. The shell 3 is preferably clear to allow penetration by UV radiation to effect the photocleavable release of compounds for bioassay. The shell 3 should also be inert and stable against a variety of organic solvents, strong acids and bases, heat, and other conditions typical of organic synthesis. The polymer coating 2 is preferably attached to the inner surface of the rigid shell 3 so that the polymer remains attached throughout the various synthesis steps. Such steps may involve the use of high temperatures (up to 100° C.), organic solvents (MEK, chloroform, etc.), strong acids and bases, and oxidizing reagents. Preferred materials for the reaction vessel shell 3 include glass, quartz, or optically and chemically compatible plastics (e.g. Teflon that is transparent to light at 300–400 nm wavelength). The polymer coating may be deposited onto the inner surface of the shell by methods conventional in the art. An example of such a method is disclosed by Garner et al. in U.S. Pat. No. 5,387,526, the disclosure of which is incorporated herein by reference.

Nominal dimensions for a preferred reaction vessel 1 may be as follows:

| | |
|---|---|
| inner diameter of shell, 3 | 1 mm |
| outer diameter of shell, 3 | 2 mm |
| length of shell, 3 | 100 mm |
| thickness of coating, 2 | 0.05 mm |

Use of the tubular reaction vessel 1 having the aforementioned nominal dimensions in solid phase chemical synthesis allows for a high output yield. For example, using TentaGel® S $NH_2$, mentioned supra as a coating, which has a vendor-published value of active sites at 0.3 µmol/mg and a density of 1.2 g/cm$^3$ for the coating, then the vessel should support roughly 2.4 µmol of compound during synthesis. This represents an ideal yield of roughly 1.2 mg based on a molecular weight of 500 g/mol.

Figure 7:
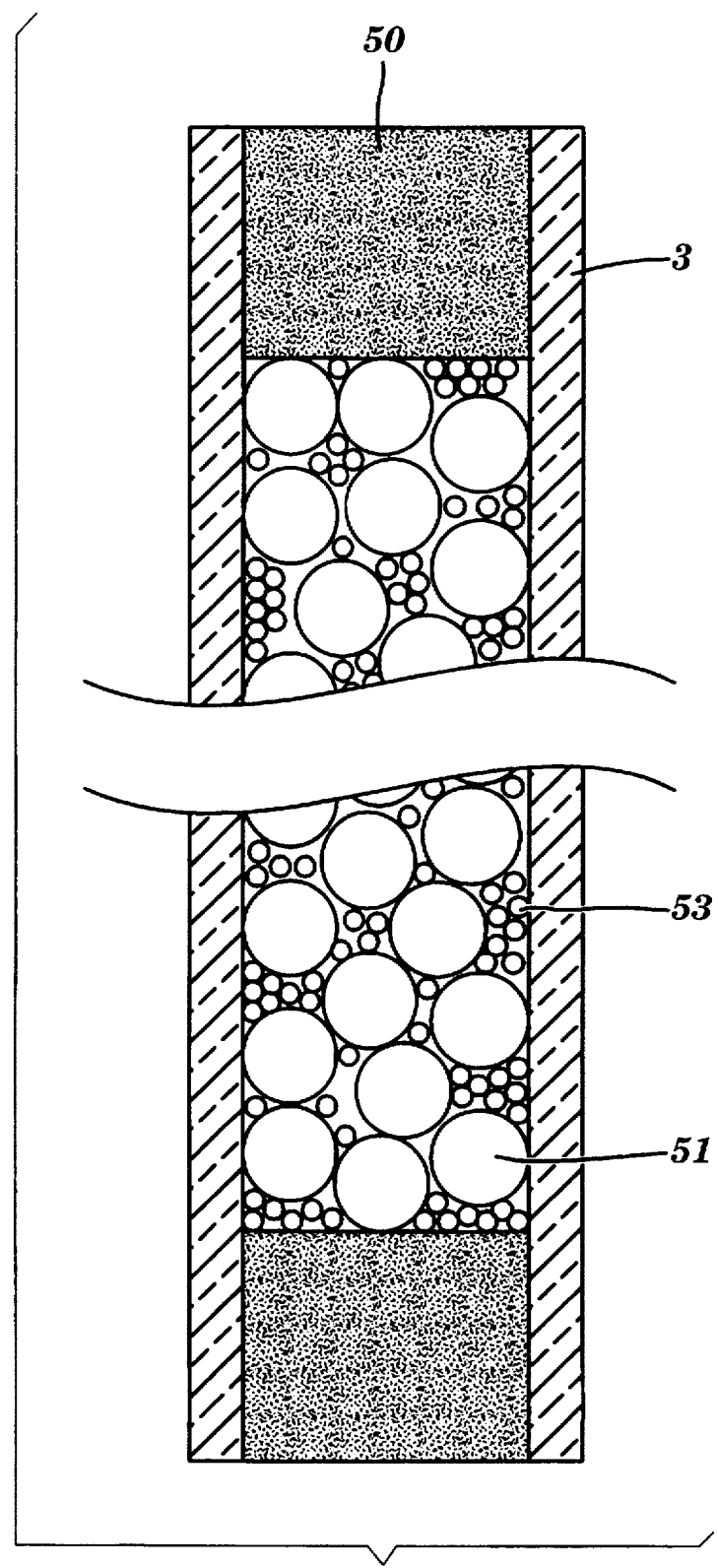
FIG. 7 depicts an isometric view of an alternative embodiment of the tubular reaction vessel having reactive polymer beads and glass beads therein.

As shown in FIG. 7, an alternative embodiment of a thin tubular reaction vessel is shown. Each of the ends of the reaction vessel is capped with a permeable frit 50, typically glass, that allows fluid to flow therethrough. In this embodiment, the reaction vessel shell 3 is filled with a mixture of glass beads 51 (300–700 μm) and reactive polymer beads 53 (100–200 μm). The glass beads 51 are disposed to allow reagents containing solvents to flow rapidly over the polymer beads 53 and through the vessel shell without causing the polymer beads to collapse into a flow-restricting aggregation. This type of reaction vessel may be constructed from commercially available materials. However, the flow and diffusion properties near any polymer bead may not be as desirable as those attainable with the coated tube depicted in FIG. 1.

Figure 8:
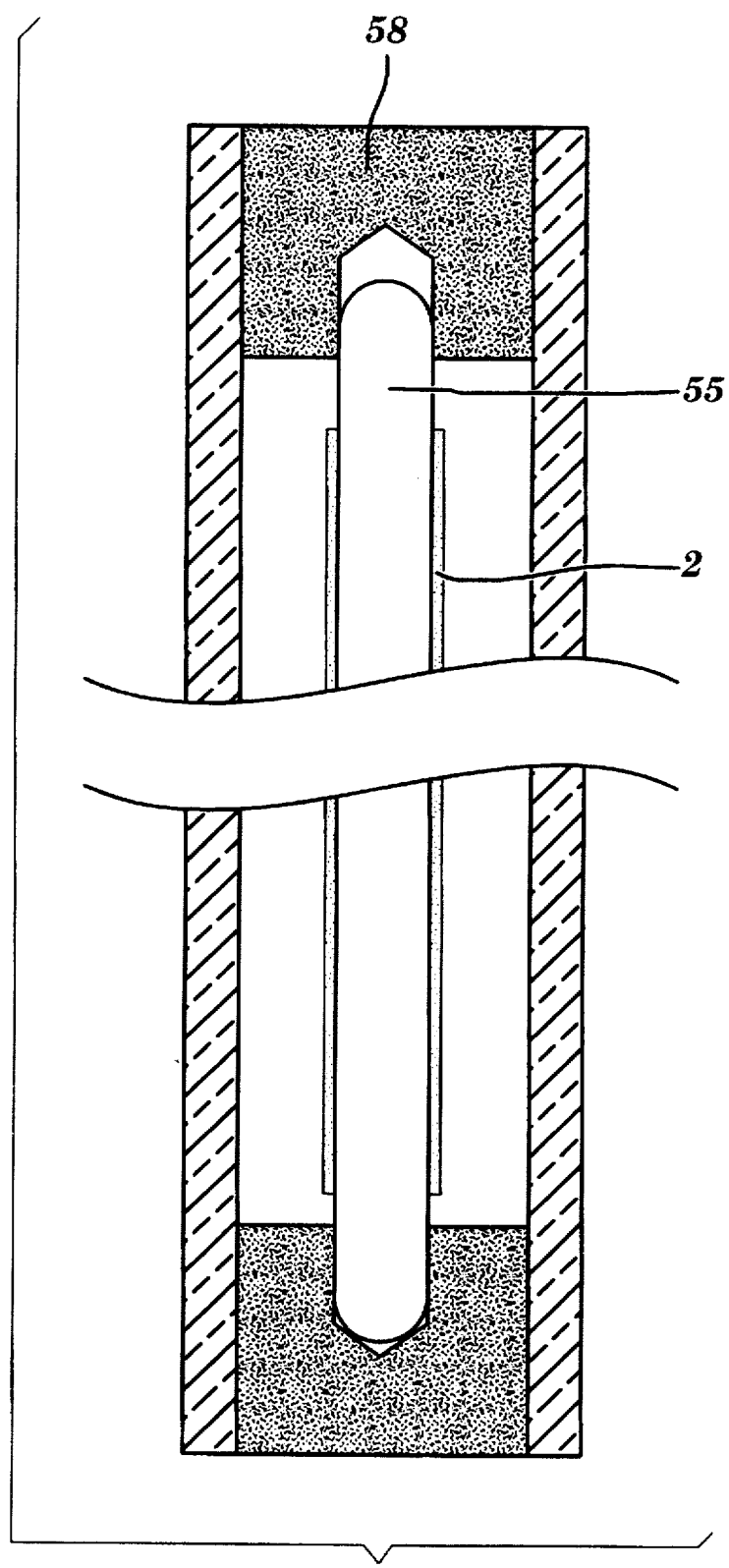
FIG. 8 depicts a sectional view of yet another embodiment of the tubular reaction vessel having a rod coaxially oriented therein coated with reactive material.

As shown in FIG. 8, another alternative embodiment of a reaction vessel is shown, incorporating a small tube or rod 55 coated with the reactive polymer-gel 2. The smaller tube or rod is coaxially oriented inside the larger reaction vessel shell 3 using alignment fixtures 58 located at each end of the vessel 1 to position the small tube or rod concentrically within the larger tube. Each alignment fixture 58 may be constructed of a glass frit. The use of the smaller tube or rod 55 allows for coating of its exterior surface, which may be more easily accomplished than coating the interior of the shell 3.

Referring again to FIGS. 1A and 1B, electronically readable indicia, preferably an optically readable bar-code 4, is preferably etched or marked in rings around the outside of the vessel to establish unique identifying indicia for each vessel. The markings or etching should be resistant to all the solvents and synthesis conditions to which the vessel will be exposed and should not contribute to any chemical contamination during synthesis. A typical bar-code covering integers from 1–1,000,000 can be accommodated within a 1 inch segment of the length of the reaction vessel 1. Since the bar-code 4 is marked in bands, its readout will be independent of the rotational orientation of the vessel 1 with respect to its central, longitudinal axis. Specific methods of rapid bar-code 4 readout are disclosed herein with reference to FIGS. 4 & 5.

Referring to FIG. 2A and 2B, an exploded view and cutaway side view of a preferred reaction chamber assembly 5 are shown with a plurality of reaction vessels 1 formed in an array inserted within the chamber. The reaction chamber 5 is designed to provide a uniform, efficient reaction environment for the reaction vessels therein. Referring to FIG. 2B, the bold arrows indicate the reagent flow entering through the chamber inlet cover 11 and eventually out the chamber outlet cover 9. The flow is made even throughout the internal cross sectional area of the chamber by use of flow diffuser 12 disposed within the chamber inlet cover 11. Each reaction vessel 1 is aligned in parallel with the flow direction when inserted into the guide array insert 6. The inlet guide cap 10 and exit guide cap 8 provide further alignment and immobilization for the reaction vessels when the chamber covers 11, 9 are fastened on the chamber body 7. A detailed view, such as that of FIG. 2C, indicates how the inlet guide cap 10 can direct reagent flow efficiently through the reaction vessel 1. The reagent flow may contain a variety of corrosive and volatile solvents that can attack most plastics and metals. Furthermore, reaction temperatures within the chamber may reach as high as 100° C. The chamber body 7 and chamber covers 9, 11 are constructed from structurally rigid materials with sufficient solvent resistance properties; borosilcate glass and highly corrosion resistant plastics are preferred materials. However, thermoformable resins such as PVDF, polyethylene, or polypropylene may also be used in some applications. Also, the guide array insert 6 and the guide caps 8, 10 may be molded or extruded using very solvent-resistant resins such as PTFE, TFE, or PVDF. The chamber covers 9, 11 are preferably sealed to the chamber body 7 through a pair of O-rings 31, 33 (FIG. 2B) which should be made of solvent-resistant materials such as KALREZ®. This type of material is manufactured by E.I. Dupont de Nemours and Company of Wilmington, Del., and is capable of withstanding a variety of solvent, high temperature and high sealing forces while maintaining thermal stability. Other sealing means, however, may also suffice. The outlet and inlet covers 9, 11 may be clamped to the chamber body 7 by any appropriate clamping mechanism (not shown). A tab structure 35, or other mark, on an outer corner of the chamber body 7 may be used as a reference for the specific locations of the respective reaction vessels 1 as arrayed in the reaction chamber 5. This reference is important for the sorting process prior to or following various reaction steps and in the sampling process for bio-assays described herein.

Figure 3:
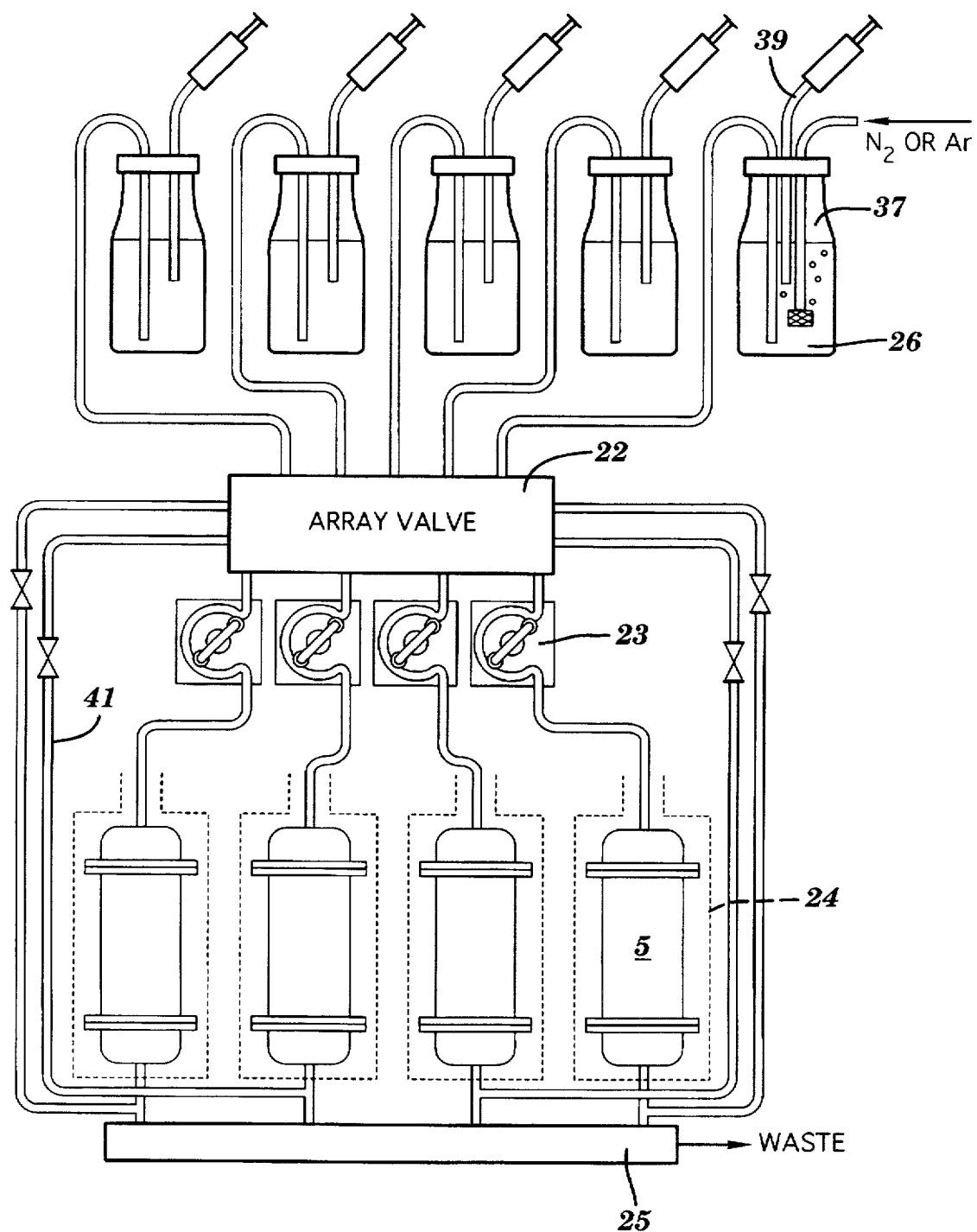
FIG. 3 depicts a schematic representation of an embodiment of a reaction system, including reagent bottles, pumps, reaction chambers and reagent switching valve-arrays.

Referring to FIG. 3, a reaction system is shown with four reaction chambers 5 installed therein. Reagent reservoirs such as bottles 26 are prepared to contain the desired quantity of solvent with the desired concentration of reagents. The reagent bottles 26 are shown as sealed with purge/sparge lines 37 inserted to allow removal of oxygen and/or equilibration with specific dissolved gases. Syringe lines 39 are shown as means for adding reagents. However, other means for adding reagents may be used. For example, solid reagents may be added and dissolved through a resealable tube in the reagent bottles 26.

The reaction system of FIG. 3 allows for a parallel method of synthesizing a large collection of compounds, the respective compounds retained in the gel phase interiors of the respective reaction vessels 1 that are contained inside each reaction chamber 5. All reaction vessels inside a given reaction chamber 5 will experience the same chemical conditions for a particular step in the synthetic process. The array valve 22 in fluid flow relationship with each reagent bottle 26 can direct a different reagent solution to each reaction chamber from any of the reagent bottles 26 shown. The array valve 22 can also facilitate a sequence of reagent exposures for a given synthetic step. Temperature-controlled enclosures 24 may surround each of the reaction chambers 5, allowing each reaction step to occur at a prescribed temperature in addition to the controlled reagent/solvent exposure. The reagent/solvent exposure is further controlled by the independent peristaltic pumps 23 each placed downstream of the array valve 22. The peristaltic pumps can control the flow rates to the corresponding reaction chambers downstream therefrom. Hence, the volumetric rate of fresh reagent/solvent communicating with the gel phase inside the reaction vessels 1, necessary for specific reactions, may be controlled by the pumps 23.

The peristaltic pumps 23 can be programmed to exchange fresh reagent/solvent into the reaction chambers and subsequently halt flow during a prescribed equilibration or "incubation" period. This allows fluid reagents adequate time to fully react with the intermediate compounds retained in the gel phase inside the reaction vessels 1. After equilibration, flow can be resumed to remove unwanted dissolved byproducts and to introduce fresh reagents. Reactions can be optimized and reagents can be used in a more efficient manner with such a programmed flow. A waste manifold 25 accepts the post-reaction effluent and maintains a closed fluid system to prevent unwanted air exposure to the reagent/solvents.

Alternatively, to further conserve on reagents while maintaining a flowing reaction environment, a recirculation fluid path 41 can be arranged for each reaction chamber. However, when using a recirculation path, care should be taken to avoid clogging of valves by any gel particles that may dislodge or precipitate from the reaction vessels. Moreover, the extent of recirculation may have to be limited due to the potential increasing concentration of reaction byproducts in the recirculating fluid. Another alternative is to provide a means of sealing the entrance and exit ports of the reaction chambers 5 so that they may be removed from the reaction system for equilibration "off-line." While such equilibration is occurring, different reaction chambers may be installed in the reaction system.

In a preferred embodiment, each reaction chamber 5 may accommodate 100 reaction vessels 1. The reaction system shown in FIG. 3 can be replicated so that groups of reaction chambers can share a set of reagent bottles. An arrangement involving as many as 100 reaction chambers is practically feasible for the construction of a large collection of compounds. Such an arrangement would utilize 10,000 reaction vessels, wherein each vessel can be involved in one of potentially 100 different synthesis steps, resulting in a high potential for diversity of the resulting chemical library. However, even with the convenient fluidics shown in FIG. 3, the task of sorting and tracking the reaction vessels in between each synthetic step could be onerous for a collection of 10,000 vessels or more.

Figure 4:
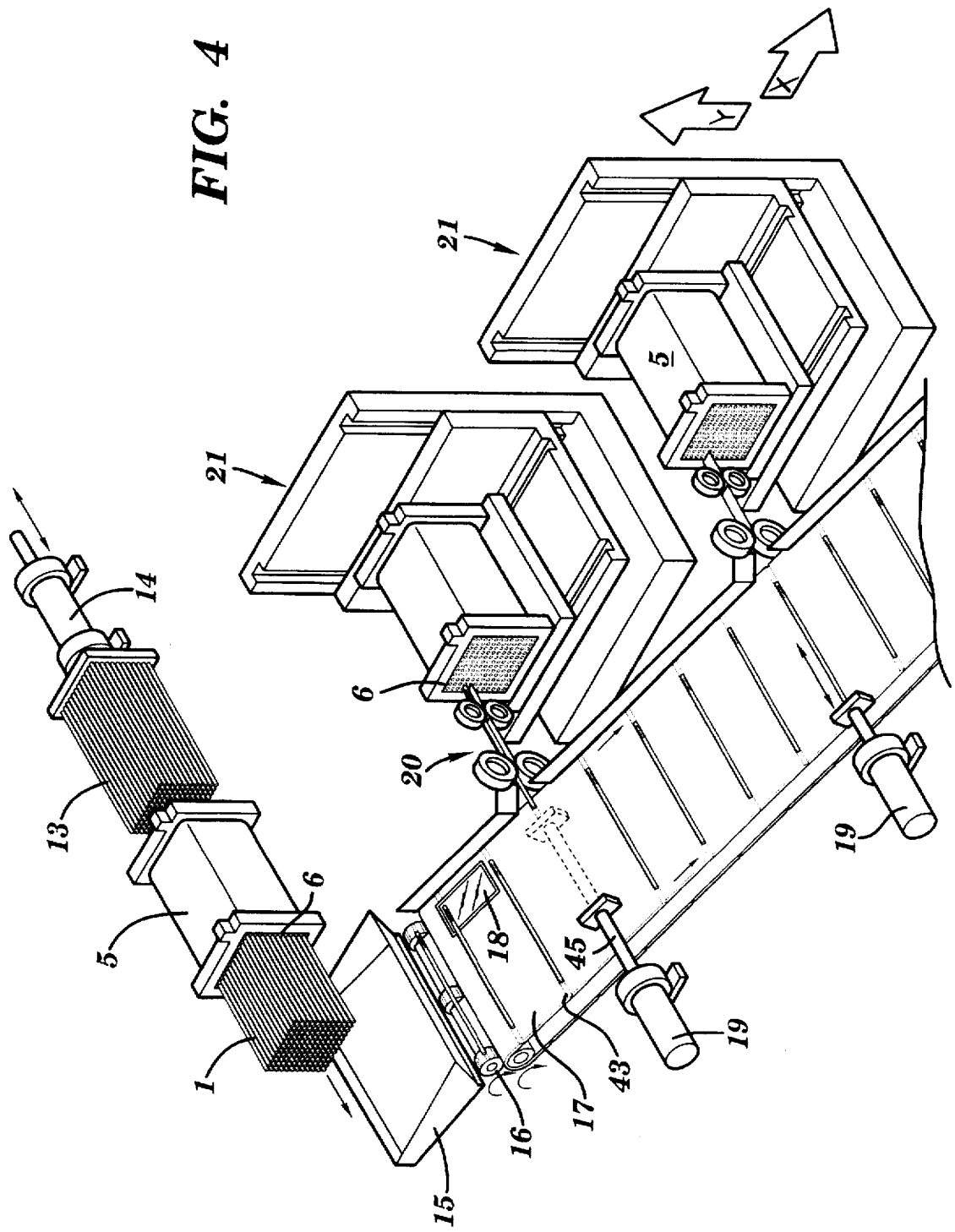
FIG. 4 depicts a schematic representation of an embodiment of a sorting means useable to perform solid phase chemical synthesis in a plurality of reaction vessels where reaction vessels are identified and moved into one or more appropriate reaction chambers for a subsequent synthetic step.

Referring to FIG. 4, a sorting means is shown, including means for tracking and transferring reaction vessels 1 from one reaction chamber to another reaction chamber in preparation for the next synthetic step. After completion of a synthetic step, the reaction chamber 5 is equilibrated with an inert solvent and carefully drained so as to avoid damage to the reactive material in the reaction vessels 1. The chamber covers and inlet guide cap are removed to allow the reaction vessels 1 to exit the chamber using an extrusion means such as an extrusion tool 13 having an array of long pins that are guided through the holes in the exit guide cap by a plunger 14. Although an extrusion tool 13 is depicted in FIG. 4, any mechanism or technique which may extrude the reaction vessels 1 from the reaction chamber may be used. The reaction vessels are deposited in a sorting hopper 15 with all the tubes oriented in the same direction. For instance, the barcoded end of the tubes is oriented towards the reaction vessel after extrusion therefrom into the hopper 15. A hopper feed 16 randomly accepts the tubular reaction vessels 1 from the hopper and transfers them to a conveyor belt 17 in fixed intervals. Alternatively, a ramp (not shown) may be used to allow the reaction vessels to roll thereon. The belt 17 may have rib structures 43 that maintain the reaction vessels 1 in fixed spacings. The reaction vessels may be released in intervals ranging from 0.1 to 1 second so that each chamber containing 100 tubes can be sorted in under 2 minutes.

Sorting of 10,000 reaction vessels 1 can be accomplished in from 20 minutes to 3.3 hours. All subsequent sorting steps including bar code reading and ejection from the belt into the appropriate new chamber may be timed to correspond with this feed rate. The bar code reader 18 is adapted to, and placed in relationship with, the belt 17 in order to read each bar coded reaction vessel 1 placed thereon. The bar code reader 18 identifies each reaction vessel as it travels within scanning distance. The bar code reader 18 is interfaced with a computer (not shown) which controls and monitors the reaction-chamber-location and identification of each reaction vessel 1. Conventional software may be used to decode the bar-code for each reaction vessel and determine the destination, e.g., the location within any reaction chamber 5 for the next reaction step for the particular reaction vessel.

One of a series of mechanical vessel directors 19, each disposed on the opposite side of belt 17 from the respective reaction chambers 5 and in alignment therewith, may then be electronically actuated to push any vessel 1 into the appropriate reaction chamber 5 when the vessel moves into the proper position. The bar code reader 18, or another optical reader, may be used to determine the location of such vessel on the belt 17 and actuate the vessel director 19 when appropriate. The vessel director 19 contains a punch 45 which, when activated, contacts the end of a reaction vessel and directs the vessel 1 into a vessel loading device 20. Vessel loading device 20 may be used within the reaction chamber 5 to carefully move any vessel 1 into the reaction chamber 5 after such vessel has been ejected from belt 17 by the vessel director 19. The reaction chambers 5 are mounted on a dual axis adjustable receiver 21 which moves along both an X and Y axis. The adjustable receiver 21 moves the reaction chamber to the appropriate location for insertion of one reaction vessel 1 at a time therein. The adjustable receiver 21 is controlled by a computer which also monitors the position of each reaction vessel within the chamber 5 mounted on the receiver 21. The reaction chambers 5 are indexed after each vessel 1 is loaded so that each chamber can be filled with reaction vessels in a deliberate fashion using the grid of holes defined by the guide array insert 6. The software and hardware required for these sorting operations may be similar to that used by manufacturing engineering groups or consultants in the clinical or diagnostic reagents and disposables industries, which is readily commercially available. After all the reaction vessels have been sorted and loaded into the reaction chambers 5, the reaction chambers 5 can be reassembled with their guide caps and chamber covers and installed in a reaction system, such as that of FIG. 3, for the next step in the combinatorial synthesis.

The present invention provides flexibility with regard to the "mix-and-split" operations performed in combinatorial synthesis. Random mix-and-split methods as disclosed in PCT Patent International Publ. No. WO 94/08051 to Still et al. are easily achieved by pushing all the vessels 1 using the extrusion tool 13 into a large hopper 15 where the reaction vessels 1 can be mixed by rotation thereof in a direction parallel to the longitudinal axis of the reaction vessels 1. Bundles of vessels 1 can be removed, randomly separated and loaded into the next reaction chamber 5 using the system of FIG. 4 or by hand. Alternatively, complex mix-and-split algorithms that systematically eliminate certain combinations or provide multiple (i.e., extra) copies of other combinations can be implemented through a preprogrammed computer-controlled function that determines which reaction vessel director 19 is activated for each reaction vessel 1. Random mix and split operations performed in combinatorial chemistry can be facilitated in large quantities by recording data, immediately prior to the placement of each reaction vessel 1 into a reaction chamber 5 or immediately subsequent to its removal therefrom, relating to the reactions performed in such reaction vessel. For example, data relating to a particular reaction, such as the reagents and/or the reaction conditions, may be recorded and stored in a database along with identifying data from an electronically readable medium on the reaction vessels, such as the bar code. In this manner, the reaction vessels may be tracked by the electronically readable indicia and the chemical recipe of compounds synthesized therein deciphered based upon reading the indicia and corresponding the same to the relevant data relating to the reactions performed. Alternatively, data relating to the reactions undergone within a particular reaction vessel may be recorded by a recording means, such as a computer. The reaction vessels then may be tracked by their particular locations within reaction chambers at every reaction stage, e.g., by placing each reaction vessel in predetermined locations within such reaction chambers at each reaction stage, and recording reaction conditions for each reaction chamber at every reaction stage. Using this technique, the chemical recipe for the compound synthesized within any reaction vessel may be determined based solely upon the location of such reaction vessel within a particular reaction chamber after the final reaction stage.

Figure 5:
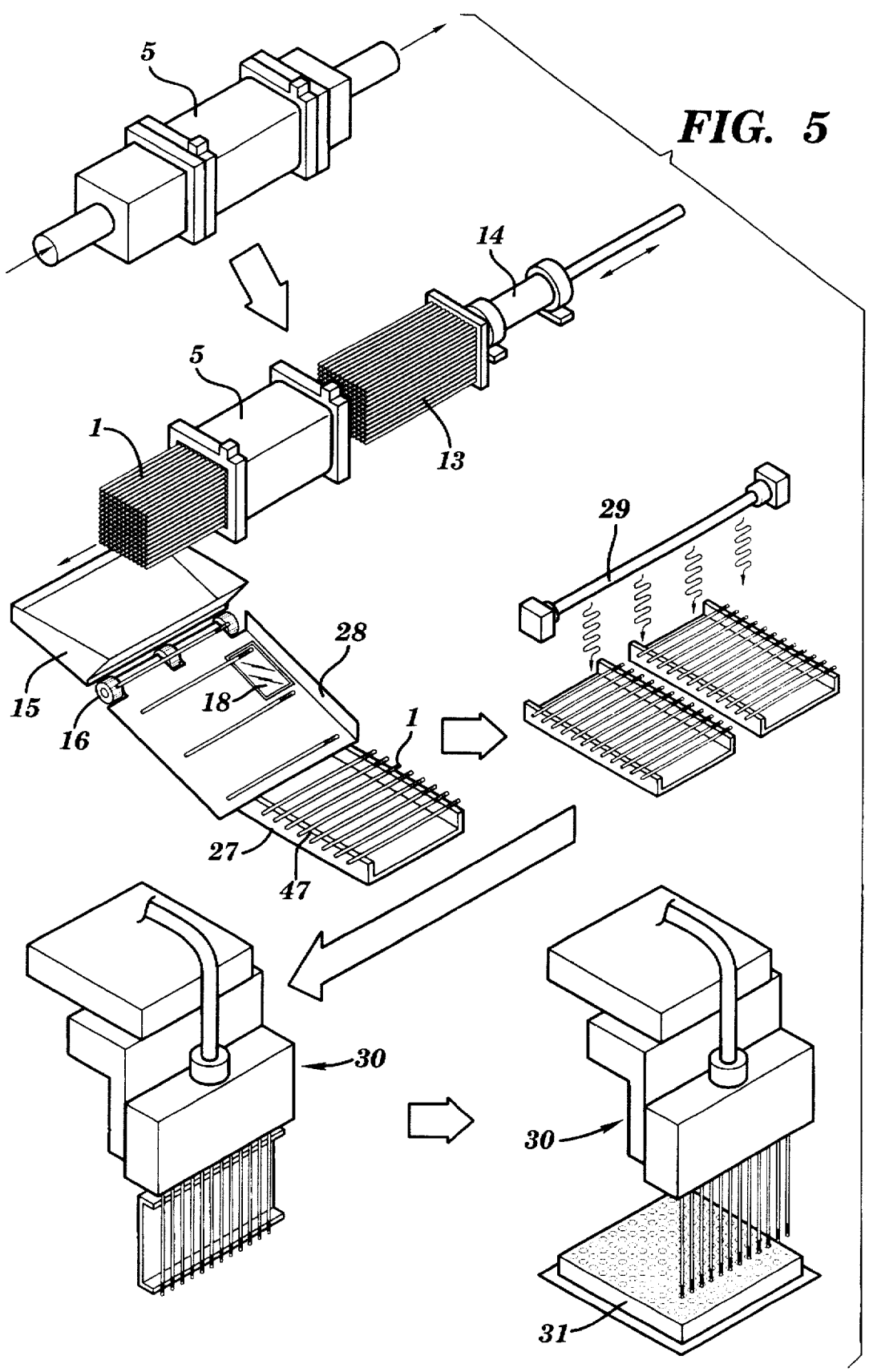
FIG. 5 depicts a schematic representation of an embodiment of a bioassay sampling system where reaction vessels are sorted onto special fixtures for photoelution of compounds and for pipetting eluent into 96-well plates using robotic pipettors.

FIG. 5 depicts a schematic of a system which shows how the compounds in the reaction vessels 1 are released and sampled into standard 96-well microtiter plates after combinatorial synthesis within the reaction vessels 1 is complete. Reaction vessels 1 are loaded into a hopper 15 using the extrusion tool 13 and plunger 14. The reaction vessels 1 may be removed from the hopper via feed mechanism 16 and loaded in order of feeding onto an alignment fixture 27, which may be designed specifically for use with the 96-well plate format, using a short ramp 28 or conveyor belt (not shown) and by mechanically moving the alignment fixture 27, preferably in increments, under the short ramp 28. A bar-code reader 18 reads the codes on the reaction vessels 1 as they roll down the ramp 28 and a computer (not shown), interfaced with the bar code reader, tracks the vessels as they are loaded onto each alignment fixture 27. One of ordinary skill in the art can readily utilize software to determine which vessels 1 are loaded in what order onto each alignment fixture 27 for screening.

The alignment fixtures contain indentations 47, preferably V-shaped, wherein the reaction vessels 1 are seated. The alignment fixtures 27 may also contain an electronically readable and/or writable indicia such as a barcode, allowing additional traceability and monitoring of each reaction vessel 1 with respect to each alignment fixture 27 and sample well 31. The reaction vessels 1 may be filled with an elution solvent before they are loaded onto the alignment fixtures. This is preferably accomplished by flushing the reaction chamber 5 with elution solvent before removing the vessels 1 therefrom and loading them into the hopper 15. However, the elution step can be performed in other ways conventional in the art.

The extrusion means such as extrusion tool 13, which is also interfaced with the computer, may be programmed to extrude only certain reaction vessels from any given reaction chamber. This controlled extrusion may be performed either after the completion of all combinatorial synthesis steps, as shown in FIG. 5, or between reaction stages during the combinatorial synthesis, as shown in the system of FIG. 4. Such controlled extrusion could facilitate sorting of the reaction vessels into the proper reaction chambers for the next reaction step.

Once the alignment fixtures 27 are loaded with reaction vessels 1, if the compounds synthesized therein were attached to the reactive polymer coating by a photo-labile covalent linker, the vessels are placed under a controlled intensity ultraviolet source 29 to detach the synthesized compound from the polymer within each such reaction vessel 1. Such photo-labile covalent linking techniques used in solid phase synthesis are described by Still et al. in PCT Patent International Publ. No. WO 94/08051. A portion of each of the bound compounds can be detached and eluted as a linear function of the ultraviolet power multiplied by exposure time when the fractional release is small. Alternatively, a portion can be detached by exposing a fractional section of a tube that has been cut up. Since microtiter plate well volumes are typically about 100 µl and desired test concentrations are usually about 1 µM, only about 0.01% release of the estimated 1–2 µmol total quantity of each compound is needed. It may be desirable to expose the entire surface of the reaction vessels to the ultraviolet light in order to optimize the release of compounds therefrom. To accomplish this, the alignment fixtures 27 may be made of a photo-transparent material and the reaction vessels may be held in sandwich fashion between two alignment fixtures. After exposing one side of each of the reaction vessels to the light, the mated alignment fixtures could then be easily flipped to allow the opposite sides of these reaction vessels to be exposed to the light. Other conventional techniques, however, for optimizing exposure may be used.

After exposure to ultraviolet light, each alignment fixture 27 may be rotated so that the reaction vessels 1 are vertically oriented. The alignment fixture 27 nominally holds the vessels in rows of 12 or columns of 8. Means for transport and fluid delivery, such as robotic pipettor 30, moves over to an alignment fixture and captures the vessels using a septum or seal-based capture mechanism (not shown), which engages the ends of the reaction vessels 1 to form a seal therewith. The arm of the robotic pipettor 30 then can move the vertically oriented reaction vessels into alignment with the wells of a target plate 31, and the elution solvent is dispensed from the vessels 1 into said wells by pressuring the vessels via the pipettor 30. The pipettor may wash out any remaining compound that has been released by the UV light by delivering additional wash solvent from a reservoir. After all the desired rows (or columns) of the 96-well plate 31 are filled using, if desired, different sets of vessels 1 from different alignment fixtures 27, plate 31 is removed and the elution solvent dried off, leaving just the sample compounds from the vessels 1 therein. Multiple compounds may be loaded into each well if desired, using additional alignment fixtures 27 and by computer-controlling the robotic pipettor 30 appropriately. Plate 31 may also contain electronically readable and/or writable indicia such as a barcode to allow for computerized tracking of compound identity for each plate and well location.

Figure 6:
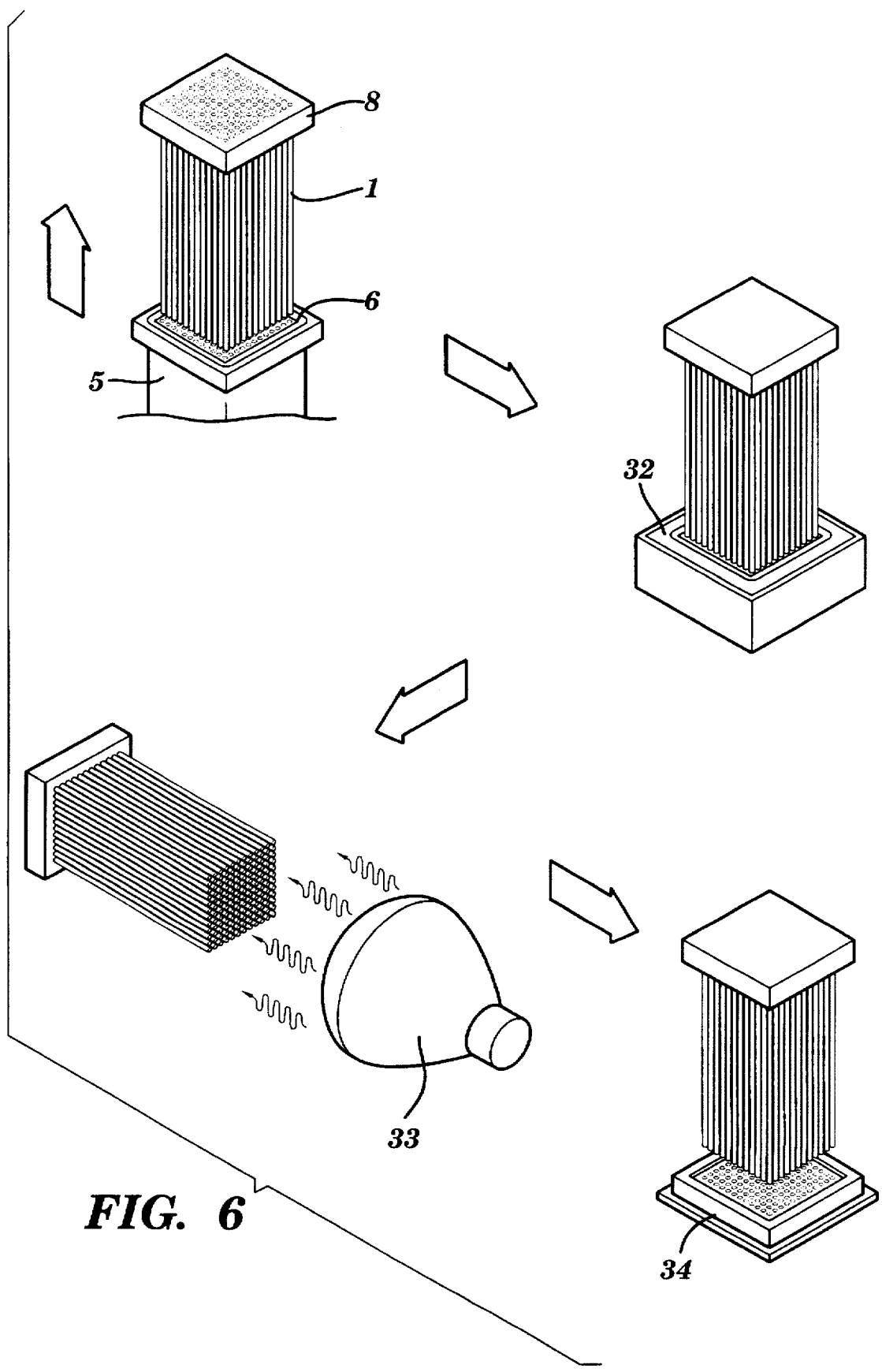
FIG. 6 depicts a schematic representation of an embodiment of another bioassay sampling system where reaction vessels are bundled directly from a reaction chamber in a dense format, dipped into an elution solvent, photoeluted with end-on illumination, and dipped into a lawn type assay plate where small eluent volumes are transferred by capillary action in the same dense pattern.

FIG. 6 depicts a schematic of an alternative, high throughput technique of sampling the synthesized compounds from the reaction vessels 1 and performing a bioassay. Rather than arranging the reaction vessels with the typical 9 mm spacing corresponding to the rows or columns of a 96-well microtiter plate as described with reference to FIG. 5, the vessels 1 may be arranged in a more dense grouping. This type of system may be used when precise volume control of the synthesized compounds is not necessary, or when moving small volume fluid samples of compounds is desired. The reaction vessels may be extracted from a reaction chamber 5 by using one of the inlet or exit guide caps 8 as a means of holding onto one end of the group of tubular reaction vessels 1. The other end of the group of reaction vessels 1 may be loaded with elution solvent by dipping into a solvent tank 32. The amount of solvent loaded, typically about 2 to about 20 µl, may be determined by capillary action.

The ends of the vessels 1 dipped into the solvent may then be exposed to ultraviolet source 33. The exposure may be adjusted to release a pre-determined portion of each compound, typically about 0.1% of that bound to the solvent-exposed polymer. The elution solvent from each reaction vessel 1 may then be transferred to a lawn bioassay plate 34 by dipping the ends of the vessels 1 therein and relying on capillary forces to deliver the compound-containing solvent. Alternatively, the small volume of solvent from each vessel 1 may be transferred by aligning the group of vessels 1 with guide cap 8, over the lawn bioassay plate 34 in a fixture, placing the entire assembly in a centrifuge (not shown) and spinning the solvent out of the tubes into the bioassay plate. The bioassay plate 34 may be adapted to have small individual wells to efficiently receive the solvent.

Use of the tubular reaction vessels 1 may also allow for the use of liquid chromatography techniques and systems for purification of the synthesized compounds prior to deposition into plates or bioassays. Compounds extracted into solvent from the vessels 1 can be easily transferred to a chromatographic system through simple tubing connectors as in FIG. 5. Purified compounds obtained from liquid chromatographs may be deposited directly into a plate or bioassay.

Although the invention has been disclosed with reference to the embodiments depicted herein, it will be apparent to one of ordinary skill in the art that various modifications and substitutions may be made to such embodiments. For example, different indicia other than bar codes may be used on the reaction vessels; various configurations for the reaction chambers may be used; various configurations may be appropriate for reaction systems using multiple reaction chambers, solvents and reagents; and various different extrusion means and sorting means may also be used. Any such modifications and/or substitutions are intended to be within the scope of the invention as defined by the following claims.

What is claimed is:

1. A method of performing chemical synthesis on solid phase reactive material contained within a plurality of tubular reaction vessels, using one or more reaction stages, resulting in a plurality of final products and employing identifying indicia to represent specific reactions and reagents utilized during said one or more reaction stages, said method comprising:

reading said identifying indicia provided for each of a plurality of tubular reaction vessels, reacting a reagent with said reactive material by flowing a reagent-containing solution through said tubular reaction vessels under particular reaction conditions, wherein said reacting is driven to completion within the reactive material by said flowing of reagent-containing solution through said tubular reaction vessels without agitation of said reactive material;

recording information concerning said reaction conditions and reagents, said information corresponding to said identifying indicia; and repeating said reading and said reacting at least once using a different reagent, thereby synthesizing chemical compounds within said tubular reaction vessels.

2. The method of claim 1 wherein said identifying indicia comprise electronically readable indicia located on said tubular reaction vessels.

3. The method of claim 2 wherein said identifying indicia comprise a bar code and said reading step is performed using a bar code reader.

4. The method of claim 1 wherein said reactive material is coated on an inside wall of said tubular reaction vessel.

5. The method of claim 1 wherein said reactive material comprises a packing disposed within said tubular reaction vessels to allow reagents to flow through said tubular reaction vessels.

6. The method of claim 1 wherein said tubular reaction vessels are insertable into a reaction chamber wherein said reacting step is performed within said reaction chamber.

7. The method of claim 6 wherein said identifying indicia comprises the location of a tubular reaction vessel within said reaction chamber.

8. The method of claim 1 wherein said tubular reaction vessels are cylindrical in shape.

9. A method of performing chemical synthesis on solid phase reactive material contained within a plurality of tubular reaction vessels, using one or more reaction stages, resulting in a plurality of final products and employing identifying indicia to represent specific reactions and reagents utilized during said one or more reaction stages, said method comprising:

reading said identifying indicia provided for each of a plurality of tubular reaction vessels, reacting a reagent with said reactive material by flowing a reagent-containing solution through said tubular reaction vessels under particular reaction conditions;

recording information concerning said reaction conditions and reagents, said information corresponding to said identifying indicia;

repeating said reading and said reacting at least once, thereby synthesizing chemical compounds within said tubular reaction vessels; and wherein said tubular reaction vessel comprises a central rod axially oriented therein, said central rod being coated with said reactive material.

10. The method of claim 9 wherein said reactive material comprises a gel.

11. A method of performing chemical synthesis on solid phase reactive material contained within a plurality of tubular reaction vessels, using one or more reaction stages, resulting in a plurality of final products and employing identifying indicia to represent specific reactions and reagents utilized during said one or more reaction stages, said method comprising:

reading said identifying indicia provided for each of a plurality of tubular reaction vessels, reacting a reagent with said reactive material by flowing a reagent-containing solution through said tubular reaction vessels under particular reaction conditions;

recording information concerning said reaction conditions and reagents, said information corresponding to said identifying indicia;

repeating said reading and said reacting at least once, thereby synthesizing chemical compounds within said tubular reaction vessels;

wherein said tubular reaction vessels are insertable into a reaction chamber, and wherein said reacting is performed within said reaction chamber; and removing said tubular reaction vessels from said reaction chamber and sorting said tubular reaction vessels by reading said identifying indicia thereon.

12. The method of claim 11 further comprising sorting said tubular reaction vessels into two or more groups, said groups subsequently being inserted into separate reaction chambers.

13. The method of claim 11 wherein said sorting comprises sorting said tubular reaction vessels into at least a first and second group, and further comprising reacting a first reagent within the tubular reaction vessels of said first group and reacting a second reagent within the tubular reaction vessels of said second group.

14. The method of claim 13 further comprising testing the synthesized chemical compounds for a particular chemical or biological activity and identifying one or more of said compounds based upon said identifying indicia and the recorded information corresponding thereto.

15. The method of claim 14 further comprising transferring a portion of each of said chemical compounds from said tubular reaction vessels into one of a plurality of assay wells.

17

16. The method of claim 13 further comprising exposing said tubular reaction vessels to a controlled intensity light source.

17. The method of claim 11 wherein said identifying indicia comprises the location of a tubular reaction vessel within said reaction chamber.

18. A method of performing chemical synthesis on solid phase reactive material contained within a plurality of tubular reaction vessels, using one or more reaction stages, resulting in a plurality of final products and employing identifying indicia to represent specific reactions and reagents utilized during said one or more reaction stages, said method comprising:

reading said identifying indicia provided for each of a plurality of tubular reaction vessels;

reacting a reagent with said reactive material by flowing a reagent-containing solution through said tubular reaction vessels under particular reaction conditions;

recording information concerning said reaction conditions and reagents, said information corresponding to said identifying indicia;

repeating said reading and said reacting at least once, thereby synthesizing chemical compounds within said tubular reaction vessels; and removing said tubular reaction vessels from said reaction chamber and randomly sorting said tubular reaction vessels into at least a first and second group.

19. The method of claim 18 further comprising reacting a first reagent within the tubular reaction vessels of said first group and reacting a second reagent within the tubular reaction vessels of said second group.

20. The method of claim 19 further comprising testing the synthesized chemical compounds for a particular chemical or biological activity and identifying one or more of said compounds based upon said identifying indicia and the recorded information corresponding thereto.

21. The method of claim 20 further comprising transferring a portion of each of said chemical compounds from said tubular reaction vessels into one of a plurality of assay wells.

22. The method of claim 19 further comprising exposing said tubular reaction vessels to a controlled intensity light source.

23. A chemical synthesis reaction vessel for performing combinatorial chemistry within a solid phase reactive material, said reaction vessel comprising:

a tubular member, said tubular member allowing reagent-containing solution to flow therethrough and having electronically readable identifying indicia thereon, said identifying indicia representing reaction conditions which have occurred or which will occur within said tubular member and representing reagents reacted or to be reacted within said tubular member; and wherein said solid phase reactive material is disposed within said tubular member such that axial flow of reagent-containing solution through said tubular member causes the reagent-containing solution to be in communication with all of said reactive material and allows reactions to be driven to completion within the reactive material without agitation of the reactive material.

24. The reaction vessel of claim 23 wherein said identifying indicia comprise a bar code.

25. The reaction vessel of claim 24 wherein said bar code is located at a first end of the tubular member.

26. The reaction vessel of claim 23 wherein said tubular member is coated with said reactive material on an inside surface thereof.

18

27. The reaction vessel of claim 26 wherein said coating of reactive material on the inside surface of said tubular member is 25–100 microns thick.

28. The reaction vessel of claim 23 wherein said tubular member comprises a photo-transparent material.

29. The reaction vessel of claim 23 wherein said reactive material comprises a packing disposed within said tubular member and said reactive vessel further comprises at least one frit located within at least one end of the tubular member, said frit allowing fluid reagents to flow therethrough while retaining said packing therewithin.

30. The reaction vessel of claim 23 wherein said tubular member comprises an elongate uniformly cylindrical vessel which can be aligned and sorted in a rolling motion.

31. The apparatus of claim 30 further comprising means for controlling flow rate through said plurality of tubular reaction vessels when disposed within said one or more reaction chambers.

32. A chemical synthesis reaction vessel for performing combinatorial chemistry comprising:

a tubular member, said tubular member allowing reagent-containing solution to flow therethrough and having electronically readable identifying indicia thereon, said identifying indicia representing reaction conditions which have occurred or which will occur within said tubular member and representing reagents reacted or to be reacted within said tubular member;

a solid phase reactive material disposed within said tubular member to allow for axial flow of reagent-containing solution through said tubular member in communication with said reactive material; and an elongate rod coaxially oriented within said tubular member, said elongate rod being coated with said reactive material.

33. The reaction vessel of claim 26 or 32 wherein said reactive material comprises a gel.

34. An apparatus for performing chemical synthesis by performing a series of reactions on solid phase reactive material comprising:

a plurality of tubular reaction vessels having electronically readable identifying indicia disposed thereon, said tubular reaction vessels containing a solid phase reactive material therein and allowing reagent-containing solution to flow therethrough, wherein said solid phase reactive material is disposed within each tubular reaction vessel such that flow of reagent-containing solution therethrough causes the reagent-containing solution to be in communication with all of said reactive material and allows reactions to be driven to completion within the reactive material without agitation of the solid phase reactive material; and one or more reaction chambers for receiving said tubular reaction vessels therein, each of said reaction chambers having an inlet disposed to allow said reagent-containing solution to flow into said reaction chamber and axially through said tubular reaction vessels disposed therein.

35. The apparatus of claim 34 further comprising one or more guide arrays insertable into said one or more reaction chambers, each guide array receiving said tubular reaction vessels therein.

36. The apparatus of claim 34 further comprising a temperature-controlled enclosure surrounding said one or more reaction chambers.

37. The apparatus of claim 34 wherein each of said tubular reaction vessels is identically sized to allow substantially even flow of reagent-containing solution therethrough.

19

38. The apparatus of claim 34 wherein each of said tubular reaction vessels comprises an elongate uniformly cylindrical vessel which can be aligned and sorted in a rolling motion.

39. An apparatus for performing chemical synthesis by performing a series of reactions on solid phase reactive material comprising:
- a plurality of tubular reaction vessels having electronically readable identifying indicia disposed thereon, said tubular reaction vessels containing a solid phase reactive material therein and allowing reagent-containing solution to flow therethrough;
- one or more reaction chambers for receiving said tubular reaction vessels therein, each of said reaction chambers having an inlet disposed to allow said reagent-containing solution to flow into said reaction chamber and axially through said tubular reaction vessels disposed therein;
- one or more guide arrays insertable into said one or more reaction chambers, each guide array receiving said tubular reaction vessels therein; and
- wherein said inlet is located within a first reaction chamber cover.

40. The apparatus of claim 39 further comprising a guide cap, said guide cap comprising a plurality of apertures therein and being located between said inlet and one of said guide arrays, wherein said apertures are aligned with said tubular reaction vessels to allow said reagent to flow from said inlet into, and axially through, said tubular reaction vessels.

41. The apparatus of claim 40 further comprising a second guide cap, said second guide cap having a plurality of apertures therein and being located between one of said guide arrays and an outlet of each of said reaction chambers, wherein said apertures are aligned with said tubular reaction vessels to allow fluid reagents to flow from said tubular reaction vessels to said outlet.

42. The apparatus of claim 41 wherein said outlet is located within a second reaction chamber cover, said first and second reaction chamber covers being located at opposite ends of a reaction chamber.

43. An apparatus for performing chemical synthesis by performing a series of reactions on solid phase reactive material comprising:
- a plurality of tubular reaction vessels having electronically readable identifying indicia disposed thereon, said tubular reaction vessels containing a solid phase reactive material therein and allowing reagent-containing solution to flow therethrough;
- one or more reaction chambers for receiving said tubular reaction vessels therein, each of said reaction chambers having an inlet disposed to allow said reagent-containing solution to flow into said reaction chamber and axially through said tubular reaction vessels disposed therein; and
- wherein said one or more reaction chambers are in fluid flow relationship to an array valve, said array valve being in fluid flow relationship with a plurality of reservoirs wherein said array valve distributes reagents from said reservoirs to the one or more reaction chambers.

44. The apparatus of claim 43 further comprising one or more pumps placed in fluid flow relationship between said array valve and said one or more reaction chambers.

45. The apparatus of claim 43 further comprising extrusion means, said extrusion means being insertable into said reaction chambers and guide array to remove said tubular reaction vessels therefrom.

20

46. The apparatus of claim 45 further comprising sorting means configured to receive tubular reaction vessels extruded from said reaction chambers.

47. The apparatus of claim 46 wherein said sorting means comprises a reader for reading said identifying indicia on said tubular reaction vessels.

48. The apparatus of claim 47 wherein said sorting means further comprises means for moving extruded tubular reaction vessels from a hopper.

49. The apparatus of claim 48 further comprising means for receiving said extruded tubular reaction vessels therein from said sorting means and for delivering said extruded reaction vessels to said reaction chamber.

50. The apparatus of claim 48 further comprising transport and fluid delivery means configured to receive reaction vessels therein and to align said reaction vessels with a plurality of wells in an assay plate.

51. The apparatus of claim 50 wherein said transport and fluid delivery means comprise a robotic pipettor.

52. The apparatus of claim 45 wherein said means for moving extruded reaction vessels comprises a ramp or a belt.

53. The apparatus of claim 52 wherein said means for moving extruded reaction vessels further comprises a vessel director disposed to move said tubular reaction vessels from said ramp or belt into a vessel loading device.

54. The apparatus of claim 53 wherein said vessel loading device receives a reaction chamber and guide array therein, said vessel loading device being moveable along a first and second axis.

55. A method of chemically synthesizing compounds for direct delivery to a biological assay comprising:
- performing a series of reaction steps on a solid phase reactive material contained within a plurality of tubular reaction vessels having identifying indicia thereon, one or more of said reaction steps being performed using reactive agents and under conditions which may be determined by electronically reading said identifying indicia;
- sorting said tubular reaction vessels into an array based upon the identifying indicia; and
- transferring synthesized biological compounds from within said array of vessels into an assay plate.

56. The method of claim 55 further comprising:
- randomly sorting said tubular reaction vessels after one of said reaction steps into at least a first group and second group of reaction vessels;
- reacting a first reagent within the reaction vessels of said first group; and
- reacting a second reagent within the reaction vessels of said second group.

57. The method of claim 56 wherein said tubular reaction vessels are sorted into more than one array and said compounds are deposited into more than one assay plate.

58. The method of claim 55 wherein said identifying indicia comprise a bar code.

59. The method of claim 55 wherein said reactive material is coated on the inside of said tubular reaction vessels.

60. The method of claim 55 wherein said solid phase reactive material comprises a packing retained within said reaction vessels by frits disposed within the ends of said reaction vessels.

61. The method of claim 55 wherein said reaction steps are performed in one or more reaction chambers configured to receive one or more of said tubular reaction vessels therein, wherein each tubular reaction vessel within a particular reaction chamber is exposed to the same chemical reagent or reaction conditions during a particular reaction step.

62. The method of claim 61 further comprising loading an elution solvent into said tubular reaction vessels.

63. The method of claim 62 wherein said tubular reaction vessels are exposed to ultraviolet radiation to release said compounds from the tubular reaction vessels.

64. The method of claim 63 wherein said compounds are deposited into said assay plate by dipping an end of a tubular reaction vessel into the surface of said assay plate.

65. A method of performing chemical synthesis on solid phase reactive material within a plurality of reaction vessels, said method comprising:

separating tubular reaction vessels into a plurality of groups and inserting each group into a different reaction chamber, said tubular reaction vessels allowing reagent-containing solution to flow therethrough and having said reactive material therein;

reacting a reagent with said reactive material within one or more of said groups of tubular reaction vessels by flowing said reagent through said reaction chambers;

recording data, said data being representative of reaction conditions and reagents within a tubular reaction vessel during said reacting step and being recorded in conjunction with information about the location of the reaction vessel in a particular chamber; and repeating said separating, reacting and recording steps at least once.

66. The method of claim 65 further comprising testing final products synthesized within said tubular reaction vessels; and identifying one or more reaction vessels having a desired final product synthesized therein.

67. The method of claim 66 further comprising evaluating said data for the one or more reaction vessels having said desired final product synthesized therein to determine the process by which said product was synthesized, so as to thereby identify said product.

68. The method of claim 66 wherein said reactive material comprises a gel.

69. A method of identifying synthesized compounds having a desired biological or chemical activity, said compounds having been synthesized during multiple reaction stages on solid phase reactive material contained within reaction vessels, said method comprising:

transferring synthesized compounds from said reaction vessels to a testing medium, said reaction vessels being tubular in shape and comprising electronically readable identifying indicia thereon representing reaction conditions which have occurred within said tubular reaction vessels;

testing for a desired biological or chemical activity the synthesized compounds transferred from said reaction vessels to said testing medium; and electronically reading the identifying indicia on the reaction vessel wherein was synthesized a compound having said desired biological or chemical activity.

70. The method of claim 69 further comprising reading recorded information wherein specific identifying indicia correspond with specific reaction histories.

71. The method of claim 70 wherein said recorded information is used to determine the structure of said compound.

72. The method of claim 71 wherein said transferring synthesized compounds from tubular reaction vessels to a testing medium comprises depositing said compounds into an assay.

73. The method of claim 72 further comprising loading an elution solvent into said reaction vessels.

74. The method of claim 73 further comprising exposing said reaction vessels to ultraviolet radiation to release said compound from said reaction vessels.

75. The method of claim 74 wherein said compounds are deposited into said assay by dipping an end of a reaction vessel into said assay.

76. The method of claim 75 wherein said identifying indicia comprise a bar code and said reading step is performed using a bar code reader.

77. The method of claim 71 or 72 wherein said reactive material comprises a gel.

78. The method of claim 77 wherein said tubular reaction vessels are configured for insertion into a reaction chamber and wherein said reacting is performed within one or more reaction chambers.

* * * * *